(12) United States Patent
Kirkpatrick et al.

(10) Patent No.: US 7,067,280 B2
(45) Date of Patent: Jun. 27, 2006

(54) HUMAN CARTILAGE GLYCOPROTEIN

(75) Inventors: Robert Kirkpatrick, King of Prussia, PA (US); Martin Rosenberg, Royersford, PA (US)

(73) Assignee: SmithKline Beecham Corp., King of Prussia, PA (US)

( * ) Notice: Subject to any disclaimer, the term of this patent is extended or adjusted under 35 U.S.C. 154(b) by 167 days.

(21) Appl. No.: 10/373,802

(22) Filed: Feb. 27, 2003

(65) Prior Publication Data

US 2003/0215847 A1 Nov. 20, 2003

Related U.S. Application Data

(62) Division of application No. 08/850,348, filed on May 2, 1997, now Pat. No. 6,576,427.

(60) Provisional application No. 60/016,532, filed on May 3, 1996.

(51) Int. Cl.
*C12N 15/00* (2006.01)

(52) U.S. Cl. .................. 435/69.1; 536/23.1; 435/23.1; 435/325; 435/320.1

(58) Field of Classification Search ............... 536/23.1; 435/325, 320.1, 69.1
See application file for complete search history.

(56) References Cited

U.S. PATENT DOCUMENTS 5,811,535 A * 9/1998 Adamou et al. ........... 536/23.5

FOREIGN PATENT DOCUMENTS

| EP | 0 805 206 | 5/1997 |
|---|---|---|
| EP | 0 823 478 | 2/1998 |
| WO | WO 98/06859 | 2/1998 |

OTHER PUBLICATIONS

Krishnan et al., J Biol Chem. Aug. 19, 1994;269(33):20971-6.*
Voet et al., (Biochemistry, John Wiley & Sons, 1990, pp. 898-900 only).*
Ren et al., 1995, Molecular and Cellular Endocrinology, vol. 113, pp. 39-51.*
Verma et al. (Nature 1997, 389: 239-242).*
U.S. Appl. No. 09/912,292, Rosen et al.
Geneseq Accession No. AAV13925. Adamou et al., Aug. 9, 1996.
Geneseq Accession No. AAW47033, Adamou et al., Aug. 9, 1996.
GenBank Accession No. T65854, Hillier et al., Feb. 20, 1995.
GenBank Accession No. U49835, Hu et al., Jul. 25, 1996.
GenBank Accession No. U58514, Hillier et al., Jul. 24, 1996.
GenBank Accession No. U58515, Grossman et al., Jul. 24, 1996.
Hu et al., J. Biol. Chem 271:19415 (Abstract Only).
GenBank Accession No. AA130121, Hillier et al., May 14, 1997.
GenBank Accession No. AA305977, Adams et al., Apr. 18, 1997.
GenBank Accession No. AA312670, Adams et al., Apr. 19, 1997.
GenBank Accession No. F06990, Auffray et al., Feb. 20, 1995.
Hu et al., "Isolation and sequence of a novel human chondrocyte protein related to mammalian members of the chitinase protein family," J Biol Chem. 271(32):19415-20 (Aug. 9, 1996).
Sekine et al. "Recognition of YKL-39, a human cartilage related protein, as a target antigen in patients with rheumatoid arthritis," Ann Rheum Dis. 60(1) 49-54 (Jan. 2001).
Knorr et al., "YKL-39 (chitinase 3-like protein 2), but not YKL-40 (chitinase 3-like protein 1), is up regulated in osteoarthristic chondrocytes," Ann Rheum Dis. 62(10).995-8 (Oct. 2003).

* cited by examiner

*Primary Examiner*—Misook Yu
(74) *Attorney, Agent, or Firm*—Human Genome Sciences, Inc.

(57) ABSTRACT

Nucleic acid sequences for HC gp-39L are provided. Methods of detecting altered expression of tissue remodeling proteins and diagnosing tissue remodeling disorders are also provided.

15 Claims, 2 Drawing Sheets

FIGURE 1A

```
   1 cagcacctgtgtggctgggggagcccagatgaagtgtggctctatcttgtatGTGAGCACACC      60
   1  Q  H  L  W  L  G  S  P  D  E  V  W  L  Y  L  V  C  E  H  T       20
  61 CACATTTCACTGCCATTATCTGGGACAGCagaaccaggtttggctcaacagatttctct        120
  21  H  I  F  T  A  I  I  W  D  S  R  T  R  F  G  S  T  D  F  S       40
 121 ttccaccatctattgcaggtgtagtggtcttgtgctcctccagggagGATCTGCCTAC         180
  41  F  H  P  S  I  A  G  V  V  L  L  L  Q  G  G  S  A  Y             60
 181 AAACTGGTTTGCTACTTTACCAACTGGTCCCAGGACCGGCAGGAACCAGGAAAATTCACC       240
  61  K  L  V  C  Y  F  T  N  W  S  Q  D  R  Q  E  P  G  K  F  T       80
 241 CCTGAGAATATTGACCCCTTCCTATGCTCTCATCTATTCATTCGCCAGCATCGAA           300
  81  P  E  N  I  D  P  F  L  C  S  H  L  I  Y  S  F  A  S  I  E      100
 301 AACAACAAGGTTATCATCAAGGACAAGAGTGAAGTGCTCTACCAGACCATCAACAGT         360
 101  N  N  K  V  I  I  K  D  K  S  E  V  M  L  Y  Q  T  I  N  S      120
 361 CTCAAAACCAAGAATCCCAAACTGAAAATTCTCTGTCCATTGGAGGGTACCTGTTTGGT       420
 121  L  K  T  K  N  P  K  L  K  I  L  S  I  G  G  Y  L  F  G         140
 421 TCCAAGGGTTCCACCTGATGGTGGATTCTTCTACATCACGCTTGGAATTCATTAACTCC       480
 141  S  K  G  F  H  P  M  V  D  S  S  T  S  R  L  E  F  I  N  S      160
 481 ATAATCCTGTTTCTGAGGAACCATAACTTTGATGGACTGGATGTAAGCTGGATCTACCCA      540
 161  I  I  L  F  L  R  N  H  N  F  D  G  L  D  V  S  W  I  Y  P      180
 541 GATCAGAAAGAAAACACTCATTTCACTGTGCTGATTCATGAGTTAGCAGAAGCCTTTCAG      600
 181  D  Q  K  E  N  T  H  F  T  V  L  I  H  E  L  A  E  A  F  Q      200
 601 AAGGACTTCACAAAATCCACCAAGGAAAGGCTTCTCTTGACTGCGGGCGTATCTGCAGGG      660
 201  K  D  F  T  K  S  T  K  E  R  L  L  L  T  A  G  V  S  A  G      220
 661 AGGCAAATGATTGATAACAGCTATCAAGTTGAGAAACTGGCAAAAGATCTGGATTTCATC      720
 221  R  Q  M  I  D  N  S  Y  Q  V  E  K  L  A  K  D  L  D  F  I      240
 721 AACCTCCTCCTTTGACTTCCATGGCTCTTGGGAAAAGCCCCTTATCACTGGCCACAAC       780
 241  N  L  S  F  D  F  H  G  S  W  E  K  P  L  I  T  G  H  N        260
 781 AGCCCTCTGAGCAAGGGTGGCAAGGGACAGAGGGCCAAGCTCCTACTACAATGTGAATAT     840
 261  S  P  L  S  K  G  W  Q  D  R  G  P  S  S  Y  Y  N  V  E  Y     280
 841 GCTGTGGGGTACTGGATACATAAGGGAATGCCATCAGAGAAGGTGGTCATGGGCATCCCC    900
 281  A  V  G  Y  W  I  H  K  G  M  P  S  E  K  V  V  M  G  I  P     300
 901 ACATATGGGCACTCCTTCACACTGGCCTCTGCAGAAACCACCGTGGGGCCCCTGCCTCT     960
```

FIGURE 1B

```
301         T  Y  G  H  S  F  T  L  A  S  A  E  T  T  V  G  A  P  A  S                                320
961    GGcCCTGGAGCTGCTGGACCCATCACAGAGTCTTcaggcttcctggcctattgagatc                                     1020
321         G  P  G  A  A  G  P  I  T  E  S  S  G  F  L  A  Y  Y  E  I                                340
1021   TGCCAGTTCCTGAAAGGAGcCAAGATCACgCGGCTCCAGGATCAGCAGGTTCCCTACgCA                                   1080
341         C  Q  F  L  K  G  A  K  I  T  R  L  Q  D  Q  Q  V  P  Y  A                                360
1081   GTCAAGGGGAACCAGTGGGGTGTATGATGTGAAGAGTATGGAGACCAAGGTTCAG                                       1140
361         V  K  G  N  Q  W  G  V  Y  D  D  V  K  S  M  E  T  K  V  Q                                380
1141   TTCTTAAAGAATTTAAACCTGGGAGCCATGATCTGGTCTATTGACATGGATGACTTC                                      1200
381         F  L  K  N  L  N  L  G  G  A  M  I  W  S  I  D  M  D  D  F                                400
1201   ACTGGCAAATCCTGCAACCAGGCCCCTTACCCTCTTGTCCAAGCAGTGAAGAGAAGCCTT                                   1260
401         T  G  K  S  C  N  Q  G  P  Y  P  L  V  Q  A  V  K  R  S  L                                420
1261   GGCTCCCTGTGAAGGATTAACTTACAGAAGCAGGCAAGATGACCTTGCTGCCTGGGGC                                     1320
421         G  S  L  *                                                                                 440
1321   CTGCTCTCTCCCAGGAATTCTCATGTGGGATTCCCCTTGCCAGGATGGCCTTTGGATCTC                                   1380
1381   TCTTCCAAGCCTTTCCTGACTTCCTCTTAGATCATAGATTGGACCTGGTTTTGTTTTCCT                                   1440
1441   GCAGCTGTTGACTTGTGCCCTGAAGTACAATaAaaaAATTcATTTTGCTCCCagT                                        1496
```

HUMAN CARTILAGE GLYCOPROTEIN

RELATED APPLICATIONS

This application is a divisional of and claims priority under 35 U.S.C. § 120 to U.S. application Ser. No. 08/850,348, filed May 2, 1997 now U.S. Pat. No. 6,576,427, which claims the benefit of U.S. Provisional Application No. 60/016,532, filed May 3, 1996 all of which are incorporated herein in their entirety.

BACKGROUND OF THE INVENTION

The generation or destruction of tissue requires constant reorganization and restructuring of the extracellular matrix (ECM) components including interstitial collagens, basement membrane collagen, fibronectin, laminin, ao'grecan, and various proteoglycans. Heinegard and Oldberg, *FASEB J.* 1989, 3, 2042–2051; Woessner *FASEB J.* 1991, 5, 214–2154. Normal types of remodeling processes include embryonic development, postpartum involution of the uterus, ovulation, wound healing, and bone and growth plate remodeling. Woessner et al. *Steroids* 1989, 54, 491–499; Weeks et al. *Biochim Biophys Acta* 1976, 445, 205–214; Lepage and Gache *EMBO J.* 1990, 9, 3003–3012; Wride and Sanders *Dev-Dyn.* 1993, 198(3) 225–39. Similar processes also occur in disease states such as joint destruction in rheumatoid and osteoarthritis, periodontia and tumor cell metastasis. Thompson and Oegema *J Bone Joint Surg.* 1979, 61, 407–16; Reynolds et al. *Adv-Dent-Res.* 1994, 8(2) 312–9. One example of these processes is the migration of macrophages to the site of inflammation as in the case of synovial tissue in rheumatoid arthritis. Cutolo et al. *Clin. and Exper. Rheum.* 1993, 11, 331–339. The ECM components are regulated, in both normal and disease states, by various exogenous and endogenous factors. For example, in tumor formation, the differentiation state of the cell can increase the rate of degradation of the ECM. Benya *Pathol. Immunopathol. Res.* 1988, 7, 51–54. Likewise, the presence of metalloproteinases or their inhibitors can alter the composition of the ECM. An imbalance of metalloproteinases and tissue inhibitors of matrix metalloproteinases (TIMP) has been shown to contribute to the pathogenesis of osteoarthritis. Dean et al. *J. Clin. Invest.* 1989, 84:678–685. Cytokines, growth factors, and the extracellular environment can all contribute to the alteration of the ECM. Tyler *Biochem J.* 1985, 227, 869–878; Dinarello *Sem Immunol.* 1992, 4, 133–145; McConnell et al. *J. Cell Biol.* 1987, 105, 1087–98.

The growth of cartilage and bone is actualized by cells such as articular chondrocytes and osteoblasts. The main function of these cells in immature tissue is the deposition and remodeling of the cartilage or bone matrix. In adult tissue, these cells maintain this matrix in order to ensure its proper function. In both cases, this encompasses secretion of the extracellular components as well as secretion of proteins involved in the turnover of the ECM.

A major species of protein secreted by these cells and involved in the turnover of the ECM are the metalloproteinases. Woessner *FASEB J.* 1991, 5, 214–2154. A new type of secretory glycoprotein has also been identified in human cartilage, osteoblasts, synovial cells, sheep and bovine oviduct and mammary cells, and macrophages. Nyrikos and Golds *Biochem J.* 1990, 268, 265–268; Hakala et al. *J. Biol. Chem.* 1993, 268(34) 25803–25810; Johansen et al. *J. Bone and Min. Res.* 1992, 7(5) 501–511; Rejman and Hurley, *Biochem. Biophys. Res. Commun.* 1988, 150, 329–334; DeSouza and Murray *Endocrinology* 1995, 136(6) 2485–2496; Hollak et al. *J. Clin. Invest.* 1994, 93, 1288–92; Arias et al. *Biol. of Reproduction* 1994, 51, 685–694. These novel mammalian proteins all share regions of significant homology to the bacterial and fungal chitinases and, therefore, are referred to herein as "chitinase-like" proteins. Chitinases are enzymes that hydrolyze glycosidic bonds. They bear a subtle similarity to lysozymes from mammals and function as endoglycosidases with a specificity for N-acetyl-glucosamine linkages. However, these types of chitin-like structures, homopolymers of N-acetyl-glucosamine, are not normally encountered in mammalian tissue.

The human cartilage glycoprotein, HC gp-39, is a protein with an apparent molecular weight of approximately 39 kDa secreted by both articular chondrocytes and synovial fibroblasts. Nyrikos and Golds *Biochem J.* 1990, 268, 265–268; Hakala et al. *J. Biol. Chem.* 1993, 268(34), 25803–25810. This protein has been described as a marker for joint injury, appearing in the blood and synovial fluid from patients diagnosed with rheumatoid arthritis. Johansen et al. *British J. of Rheumatology* 1993, 32, 949–955. The gene encoding this protein has been cloned and is expressed specifically in cartilage and synovial cells of rheumatic joints. Hakala et al. *J. Biol. Chem.* 1993, 268(34), 25803–25810. The protein YKL-40 has also been identified as one of the major secretory products of cultured human osteoblastic cells (osteocarcinoma cell line MG-63) expressed in response to 1,25-dihydroxyvitamin D3 stimulation. Johansen et al. *J. Bone and Min. Res.* 1992, 7(5), 501–511; Johansen et al. *Br. J. Rheumatol.* 1993, 32, 949–55. The N-terminal portion of YKL-40 was sequenced and found to be identical to HC gp-39. Upon further sequencing, YKL-40 and HC gp-39 were found to be identical.

Chitotriosidase is an enzyme which has been identified as a member of this "chitinase-like" family. Renkema et al. *J. Biol Chem.* 1995, 27C, 2198–2202; Hollak et al. *J. Clin. Invest.* 1994, 93, 1288–92. This protein also has an apparent molecular weight of 39 k-Da and shares N-terminal homologies with HC gp-39, the bovine mammary protein, and several bacterial chitinases. Activity of this enzyme was originally detected from cells of patients afflicted with Gaucher Disease (GD). Gaucher Disease is an inherited deficiency in the activity of glucocerebrosidase, a lysosomal hydrolase. This defect results in an accumulation of glucosylceramide (glucocerebroside) in the lysosomes of macrophages. Accumulation of lipid-laden macrophages results in hepatosplenomegaly, bone lesions, and neurological anomalies. After morphological differentiation of monocytes into macrophages in culture, the cells begin to produce and secrete increasing amounts of chitotriosidase. This increase is, on average, 600 times greater in GD patients than in patients with other pathological conditions. The elevation in chitotriosidase activity can be effectively reduced, however, upon initiation of enzyme supplementation therapy. Unlike the other members of the chitinase-like family, chitotriosidase has chitolytic activity. Like the bacterial enzyme, it has the ability to degrade chitin azure, a polymer of beta-1-4-linked N-acetylglucosamine moieties.

A new lymphocyte-associated protein of the chitinase-like family, referred to as HC gp-39L, has now been identified. HC-gp39L protien is believed to be involved in tissue remodeling in the mammalian cell and thus serve as useful tools in the development of therapeutics and diagnostics for tissue remodeling disorders.

SUMMARY OF THE INVENTION

In accordance with one aspect of the present invention, there is provided a novel mature polypeptide which is HC gp-39L, as well as biologically active and diagnostically or therapeutically useful fragments, analogs and derivatives thereof. The polypeptide of the present invention is of human origin.

In accordance with another aspect of the present invention, there are provided isolated nucleic acid molecules encoding human HC gp-39L, including mRNAs, DNAs, cDNAs, genomic DNAs as well as analogs and biologically active and diagnostically or therapeutically useful fragments thereof.

In accordance with yet a further aspect of the present invention, there is provided a process for producing HC gp-39L by recombinant techniques comprising culturing, recombinant prokaryotic, and/or eukaryotic host cells, containing a human nucleic acid sequence of HC gp-39L, under conditions promoting expression of these proteins and subsequent recovery of these proteins.

In accordance with yet a further aspect of the present invention, there is provided a process for utilizing HC gp-39L polypeptide, for therapeutic purposes, for example, in the treatment of tissue remodeling disorders.

In accordance with yet a further aspect of the present invention, there is provided a process for targeting HC gp-39L located on the surface of lymphocytes with specific antibodies, for therapeutic purposes, such as the treatment of autoimmune or tissue remodeling disorders.

In accordance with yet a further aspect of the present invention, there is provided a process for utilizing HC gp-39L polypeptide for diagnostic purposes, for example, in the diagnosis of tissue remodeling disorders.

These and other aspects of the present invention should be apparent to those skilled in the art from the teachings herein.

BRIEF DESCRIPTION OF THE DRAWINGS

FIGS. 1A–1B provide the polynucleotide coding sequence (SEQ ID NO: 1) and deduced amino acid sequence (SEQ ID NO: 2) of the polypeptide HC gp-39L.

DETAILED DESCRIPTION OF THE INVENTION

In accordance with one aspect of the present invention, there is provided an isolated nucleic acid sequence (SEQ ID NO: 1) which encodes the chitinase-like protein HC gp-39L (HC gp-39 like). The deduced amino acid sequence of this protein (SEQ ID NO: 2) is shown in FIGS. 1A–1B. Further, HC gp-39L has been isolated from lymphocytes and has been found to share 51% amino acid identity (68% amino acid similarity) with the chitinase-like protein HC gp-39, including, the conserved chitinase-like domains and cysteine motif. However, HC gp-39L differs from the other chitinase-like proteins in that the cDNA extends past the homology with HC gp-39 and chitotriosidase producing an N-terminal extension.

The nucleic acid sequences of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes HC gp-39L protein may be identical to the coding sequence shown in FIGS. 1A–1B or may be a different coding sequence which coding sequence, as a result of the redundancy or degeneracy of the genetic code, encodes the same protein as the DNA of FIGS. 1A–1B.

The present invention includes polynucleotides encoding the same mature polypeptide as shown in FIGS. 1A–1B. Further, the inventions includes variants of such polynucleotides that encode a fragment, derivative or analog, of the polypeptides of FIGS. 1A–1B. Among variants in this regard are variants that differ from the aforementioned polynucleotides by nucleotide substitutions, deletions or additions. The substitutions, deletions or additions may involve one or more nucleotides. The variants may be altered in coding, or non-coding regions or both. Alterations in the coding regions may produce conservative amino acid substitutions, deletions or additions.

Variants of the invention may have a sequence that occurs in nature or they may have a sequence that does not occur naturally. As herein above indicated, the polynucleotide may have a coding sequence which is a naturally occurring allelic variant of the coding sequences shown in FIGS. 1A–1B. As known in the art, an allelic variant is an alternate form of a polynucleotide sequences which may have a substitution, deletion or addition of one or more nucleotides.

Among the particularly preferred embodiments of the inventions in this regard are polynucleotides encoding polypeptides having the amino acid sequences of HC gp-39L set out in FIGS. 1A–1B; variants, analogs, derivatives and fragments thereof, and fragments of the variants, analogs and derivatives.

Further particularly preferred in this regard are polynucleotides encoding HC gp-39L variants, analogs, derivatives and fragments, and variants, analogs and derivatives of the fragments, which have the amino acid sequence of HC gp-39L polypeptide of FIGS. 1A–1B in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of HC gp-39L. Also especially preferred in this regard are conservative substitutions. Most highly preferred are polypeptides having the amino acid sequence of FIGS. 1A–1B, without substitutions.

Further preferred embodiments of the invention are polynucleotides that are more than 85% identical to a polynucleotide encoding, HC gp-39L polypeptide having the amino acid sequence set out in FIGS. 1A–1B, or variants, close homologs, derivatives and analogs thereof, as described above. Alternatively, most highly preferred are polynucleotides that comprise a region that is more than 85% identical to a polynucleotide encoding HC gp-39L polypeptide of FIGS. 1A–1B. In this regard, polynucleotides more than 90% identical to the same are particularly preferred, and among these particularly preferred polynucleotides, those with 95% or more identity are especially preferred. Furthermore, those with 97% or more identity are highly preferred among those with 95% or more identity, and among these those with 98% or more and 99% or more identity are particularly highly preferred, with 99% or more being the more preferred.

Also particularly preferred in this regard are polynucleotides encoding a polypeptide having the amino acid sequence of HC gp-39L set out in FIGS. 1A–1B. As set out elsewhere herein, the polynucleotide may encode the polypeptide in a continuous region or in a plurality of two or more discontinuous exons, and it may comprise additional regions as well, which are unrelated to the coding region or regions.

Most highly preferred in this regard are polynucleotides that comprise a region that is more than 85% identical to the HC gp-39L-encoding portion of the polynucelotide set out in FIGS. 1A–1B. Alternatively, most highly preferred are polynucleotides that comprise a region that is more than 85% identical to the HC gp-39L-encoding portion set forth in FIGS. 1A–1B. Among such polynucleotides, those more than 90% identical to the same are particularly preferred, and, among these particularly preferred polynucleotides, those with 95% or more identity are especially preferred. Furthermore, those with 97% or more identity are highly preferred among those with 95% or more identity, and among these those with 98% or more and 99% or more identity are particularly highly preferred, with 99% or more being the more preferred of these.

The present invention also includes polynucleotides in which the sequence encoding the mature polypeptide is fused in the same reading frame to additional sequences. Such sequences include signal sequences, which facilitate transport of the nascent protein into the endoplasmic reticulum, pro-sequences that are associated with inactive precursor forms of the polypeptide, which may facilitate trafficking of the protein in a cell or out of a cell or may improve persistence of the protein in a cell or in an extracellular compartment. Such sequences also may be added to facilitate production and purification, or to add additional functional domains, as discussed elsewhere herein.

A further preferred embodiment is an HC gp-39L polynucleotide sequence comprising a Met codon upstream (5') of the 5' sequence in SEQ ID NO:1. It is most preferred that the Met codon be part of a continuing open reading frame as that encoding the polypeptide of FIGS. 1A–1B (SEQ ID NO:2). Using the sequence of HC gp-39L of SEQ ID NO:1 skilled artisans can obtain such upstream or other upstream sequences by making primers to perform amplification using routine methods. Preferred primers useful to derive upstream sequences are obtained from the sequence: 5'-cag-cacctgtggctggggagcccagatgaagtgtggctctatcttgtaTGTGAGC ACACCCACATTTTCACTGCCATTATCTGGGACAGC agaaccaggtttggctcaacagat-3'(SEQ ID NO:3)

Fragments of this sequence are also useful, preferably fragments of about 15–50 nucleotides in length, and most preferably 20–25 nucleotides in length.

The present invention further relates to the HC gp-39L polypeptide which has the deduced amino acid sequence (SEQ ID NO: 2) of FIGS. 1A–1B, as well as fragments, analogs and derivatives of such polypeptide.

The terms "fragment," "derivative" and "analog" when referring, to the polypeptide of FIGS. 1A–1B, means a polypeptide which retains essentially the same biological function or activity as such polypeptide. Thus, an analog includes a proprotein which can be activated by cleavage of the proprotein portion to produce an active mature polypeptide. The polypeptide of the present invention may be a recombinant polypeptide, a natural polypeptide or a synthetic polypeptide, preferably a recombinant polypeptide.

The fragment, derivative or analog of the polypeptide of FIGS. 1A–1B may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptide and nucleic acid sequences of the present invention are preferably provided in an isolated form, and preferably are purified to homogeneity. The term "isolated" means that the material is removed from its original environment (e.g., the natural environment if it is naturally occurring). For example, a naturally-occurring nucleic acid sequence or polypeptide present in a living animal is not isolated, but the same nucleic acid sequence or polypeptide, separated from some or all of the coexisting, materials in the natural system, is isolated. Such nucleic acid sequences could be part of a vector and/or such nucleic acid sequences or polypeptides could be part of a composition, and still be isolated in that such vector or composition is not part of its natural environment.

The present invention also relates to vectors which include one of the nucleic acid sequences of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying HC gp-39L gene. The culture conditions, such as temperature, pH and the like, are those previously used with the host cell selected for expression, and will be apparent to the ordinarily skilled artisan.

The nucleic acid sequences of the present invention may be employed for producing polypeptides by recombinant techniques. The nucleic acid sequences may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The DNA sequence of HC gp-39L can be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the $E.\ coli$ lac or trp, the phage lambda $P_L$ promoter and other promoters known to control expression of genes in prokaryotic or eukaryotic cells or their viruses. The expression vector also contains a ribosome binding, site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli, Streptomyces, Salmonella typhimurium*; fungal cells, such as yeast; insect cells such as *Drosophila S2* and *Spodoptera Sf9*; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as described above. The constructs comprise a vector, such as a plasmid or viral vector, into which a sequence encoding HC gp-39L has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lac, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., *Basic Methods in Molecular Biology*, (1986)).

The constructs in host cells can be used in a conventional manner to produce the gene product encoded by the recombinant sequence. Alternatively, polypeptides can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., *Molecular Cloning: A Laboratory Manual, Second Edition*, Cold Spring Harbor, N.Y., (1989), the disclosure of which is hereby incorporated by reference.

Transcription of the DNA encoding a protein by higher eukaryotes is increased by inserting an enhancer sequence into the vector. Enhancers are cis-acting elements of DNA, usually about from 10 to 300 bp that act on a promoter to increase its transcription. Examples including, the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting, transformation of the host cell, e.g., the ampicillin resistancegene of *E. coli* and *S. cerevisiae* TRPI gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant proteins. Examples of mammalian expression systems include the COS-7 lines of monkey kidney fibroblasts, described by Gluzman *Cell* 1981, 23, 175, and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

Polypeptides can then be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

It is now believed that the chitinase-like proteins, particularly HC gp-39L are involved in issue remodeling. HC gp-39, HC gp-39L and human chitotriosidase are all homologous to microbial chitinases. In particular all three proteins share a similar cysteine motif and homology to the active site of microbial chitinases. Accordingly, these proteins can be used in the development of treatments for tissue remodeling diseases and in the diagnosis of these diseases.

Based on the homology with HC gp-39, HC gp-39L is believed to be a product of macrophages. Primary human monocytes, activated to become macrophages through adherence to plastic, secrete high levels of HC gp-39 into the culture media. In addition, the induction of HC gp-39 expression has been correlated with the differentiation of myeloid cell lines HL60 and U937 toward a macrophage lineage by induction with phorbol ester. HC gp-39 message can be detected in human atherosclerotic plaques derived from endarterectomies. Accordingly, it is believed that HCgp-39 functions in various tissues undergoing extensive remodeling, including, those associated with rheumatoid arthritis and atherosclerosis where macrophages play an important role. Further, rHC gp-39 was shown to stimulate in vitro smooth muscle cell migration, indicative of involvement in the remodeling processes occurring in diseased arteries.

The tissue-specific expression pattern of HC 9p-39L has also been determined. HC gp-39L is expressed specifically in lymphocyte cell lines which is consistent with tissues from which HC gp-39L is found. In addition, human multiple tissue Northern blots show that HC gp-39L message is found at the highest levels in thymus and spleen, which also consistent with lymphocyte-specific expression. HC gp-39L protein was detected by western blot using polyclonal antiserum multiple produced from rabbits immunized with a fusion construct containing a partial HC gp-39L protein. HC gp-39L protein is associated with the membrane fraction of the cells and is not secreted into the media. Accordingly, it is believed that HCgp-39L functions as a cell surface lymphocyte marker for activated lymphocytes. HC gp-39L is therefore a useful target for inflammatory or tissue remodeling diseases involving T-cell or B-cell activation such as rheumatoid arthritis.

HC gp-39L proteins can also be used in the production of antibodies. The proteins, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of a Fab expression library. Various procedures known in the art may be used for the production of such antibodies and fragments.

Antibodies generated against these proteins can be obtained by direct injection of the protein into an animal, preferably a nonhuman. The antibody so obtained will then bind the protein itself. In this manner, even a sequence encoding only a fragment of the protein can be used to generate antibodies binding the whole native protein. Such antibodies can then be used to isolate these proteins from tissue expressing these proteins.

For preparation of monoclonal antibodies, any technique which provides antibodies produced by continuous cell line cultures can be used. Examples include the hybridoma technique (Kohler and Milstein *Nature* 1975, 256, 495–497), the trioma technique, the human B-cell hybridoma technique (Kozbor et al. *Immunology Today* 1983, 4, 72), and the EBV-hybridoma technique to produce human monoclonal antibodies (Cole et al. in *Monoclonal Antibodies and Cancer Therapy*, Alan R. Liss, Inc., 1985, pp. 77–96).

Techniques described for the production of single chain antibodies (U.S. Pat. No. 4,946,778) can be adapted to produce single chain antibodies to immunogenic HC gp-39L protein product. Also, transgenic mice may be used to express humanized antibodies to immunogenic HC gp-39L protein products.

This invention is also related to the use of HC gp-39L as a diagnostic. Detection of a mutated form of HC gp-39L will allow a diagnosis of a tissue remodeling disease such as rheumatoid arthritis or atherosclerosis.

Individuals carrying mutations in one or more of these HC gp-39L proteins may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature 1986, 324, 163–166) prior to analysis. RNA or cDNA may also be used for the same purpose. As an example, PCR primers complementary to the nucleic acid encoding HC gp-39L can be used to identify and analyze mutations in this protein. For example, deletions and insertions can be detected by a change in size of the amplified product in comparison to the normal genotype. Point mutations can be identified by hybridizing amplified DNA to radiolabeled RNA or alternatively, radiolabeled antisense DNA sequences. Perfectly matched sequences can be distinguished from mismatched duplexes by RNase A digestion or by differences in melting temperatures.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting, or partial melting temperatures (see, e.g., Myers et al. *Science* 1985, 230, 1242). Sequence changes at specific locations may also be revealed by nuclease protection assays, such as RNase and S I protection or the chemical cleavage method (e.g., Cotton et al. *PNAS USA* 1985, 85, 4397–4401).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of HC gp-39L protein in various tissues. Assays used to detect levels of such protein in a sample derived from a host are well-known to those of skill in the art and include radioimmunoassays, competitive-binding assays, Western Blot analysis and preferably an ELISA assay. An ELISA assay initially comprises preparing an antibody specific to a HC gp-39L protein, preferably a monoclonal antibody. In addition, a reporter antibody is prepared against the monoclonal antibody. To the reporter antibody is attached a detectable reagent such as radioactivity, fluorescence or in this example a horseradish peroxidase enzyme. A sample is removed from a host and incubated on a solid support, e.g., a polystyrene dish, that binds the proteins in the sample. Any free protein binding sites on the dish are then covered by incubating with a non-specific protein like BSA. Next, the monoclonal antibody is incubated in the dish during which time the monoclonal antibodies attach to HC gp-39L protein attaches to the polystyrene dish. All unbound monoclonal antibody is washed out with buffer. The reporter antibody linked to horseradish peroxidase is now placed in the dish resulting in binding of the reporter antibody to any monoclonal antibody bound to HC gp-39L. Unattached reporter antibody is then washed out. Peroxidase substrates are then added to the dish and the amount of color developed in a given time period is a measurement of the amount of HC gp-39L protein present in a given volume of patient sample when compared against a standard curve.

A competition assay may be employed wherein antibodies specific to HC gp-39L protein are attached to a solid support and labeled protein and a sample derived from the host are passed over the solid support and the amount of label detected attached to the solid support can be correlated to a quantity of HC gp-39L protein in the sample.

The following examples are provided for illustrative purposes only and are not intended to limit the invention.

EXAMPLES

Example 1

Expression of HC gp-39 in vitro

Recombinant HC gp-39 was produced in vitro by transfecting an expression vector containing the cDNA into CHO cells and selecting stable cell lines.

The full length HC gp-39 gene was cloned into CDN in two pieces; a 660 bp Sac II-Bst EII fragment plus a 678 bp Bst EII-Bcl fragment, ligated together with the CDN vector cut with Sac II-Bcl I. This construct was transfected into CHO ACC 317 Cells by standard methods. Specifically, 20 mg of the HC gp-39 plasmid construct was linearized by restriction digestion and electroporated into $1.25 \times 10^7$ cell in 1 ml. Cells were seeded at a density of $2.5 \times 10^3$ cells per well and selected in minimal media in the absence of nucleosides. Secreted protein was recovered from the conditioned media and purified using Q sepharose flow through, S sepharose capture and sized on Suprose 12. The resulting material was greater than 95% pure as determined by Coomassie blue staining. HC gp-39L can also be expressed as described in this Example 1.

Example 2

Assay for Smooth Muscle Migration

Smooth muscle migration was measured in a chamber divided by a semi-permeable filter to which rHC gp-39 (2.3–766 mg/ml) was bound on one side. On the other side, human fetal smooth muscle cells were cultured. The extent to which cells migrated into the filter was monitored calorimetrically (optical density). rHC gp-39 elicited a stronger migration response in this assay than PDGF, a known stimulator of smooth muscle migration. This assay in this Example I can also be readily used for analysis of HC gp-39L.

Example 3

Production of Polyclonal Antibodies Generated Against HC gp-39L

A partial HC gp-39L protein has been expressed in *E. coli* and used to generate polyclonal antiserum. A 1461 bp NdeI-XhoI cDNA fragment of HC gp-39L was cloned in frame as a fusion with an N-terminal His tag, in the Pet 16B vector system (Novagen). These constructs were transformed into *E. coli* through standard methods. The cells were propagated, lysed, and the protein purified by nickel affinity chromatography. The purified fusion protein was used to immunize rabbits for the production of polyclonal antiserum.

Example 4

HC gp-39L is Associated with the Membrane Fraction of Lymphocytes

Polyclonal antiserum was used to detect HC gp-39L protein on Western blots. Protein is detected in whole cell lysates of lymphocytes. It is also detected in the membrane fraction, but is not associated with the cytoplasmic fraction or secreted into the media. HC gp-39L may function as a cell surface lymphocyte marker for a subset of activated lymphocytes (inflammatory or tissue remodeling diseases) and be detected by FACS analysis, a secondary detection method known to those of skill in the art.

What is claimed:

1. An isolated polynucleotide comprising a nucleic acid sequence selected from the group consisting of:
   (a) the nucleic acid sequence of SEQ ID NO:1; and
   (b) a nucleic acid sequence encoding the polypeptide of SEQ ID NO:2.

2. The isolated polynucleotide of claim 1, wherein said nucleic acid sequence is the nucleic acid sequence of SEQ ID NO:1.

3. The isolated polynucleotide of claim 1, wherein said nucleic acid sequence is a nucleic acid sequence encoding the polypeptide of SEQ ID NO:2.

4. The isolated polynucleotide of claim 1, which is DNA.

5. The isolated polynucleotide of claim 1, which is RNA.

6. The isolated polynucleotide of claim 1, further comprising a heterologous nucleic acid molecule.

7. The isolated polynucleotide of claim 1, wherein said polynucleotide is operably associated with a heterologous regulatory sequence.

8. A vector comprising the isolated polynucleotide of claim 1.

9. A vector comprising the isolated polynucleotide of claim 1, operatively linked to an expression control sequence.

10. An isolated host cell comprising the isolated polynucleotide of claim 1.

11. An isolated host cell transformed with the vector of claim 8.

12. An isolated host cell transformed with the vector of claim 9.

13. A process for producing a polypeptide comprising culturing the host cell of claim 10 under conditions such that the polypeptide encoded by said nucleic acid sequence is expressed and recovering said polypeptide.

14. A process for producing a polypeptide comprising culturing the host cell of claim 11 under conditions such that the polypeptide encoded by said nucleic acid sequence is expressed and recovering said polypeptide.

15. A process for producing a polypeptide comprising culturing the host cell of claim 12 under conditions such that the polypeptide encoded by said nucleic acid sequence is expressed and recovering said polypeptide.

* * * * *

SEQUENCE LISTING

<160> NUMBER OF SEQ ID NOS: 3

<210> SEQ ID NO 1
<211> LENGTH: 1496
<212> TYPE: DNA
<213> ORGANISM: Homo sapiens

<400> SEQUENCE: 1

```
cagcacctgt ggctggggag cccagatgaa gtgtggctct atcttgtatg tgagcacacc      60
cacattttca ctgccattat ctgggacagc agaaccaggt ttggctcaac agatttctct     120
ttccacccat ctattgcagg tgtagtggtc ttgctgcttc tccagggagg atctgcctac     180
aaactggttt gctactttac caactggtcc caggaccggc aggaaccagg aaaattcacc     240
cctgagaata ttgaccccct cctatgctct catctcatct attcattcgc cagcatcgaa     300
aacaacaagg ttatcatcaa ggacaagagt gaagtgatgc tctaccagac catcaacagt     360
ctcaaaacca gaatcccaa actgaaaatt ctcttgtcca ttggagggta cctgtttggt      420
tccaaagggt tccaccctat ggtggattct tctacatcac gcttggaatt cattaactcc     480
ataatcctgt ttctgaggaa ccataacttt gatggactgg atgtaagctg gatctaccca     540
gatcagaaag aaaacactca tttcactgtg ctgattcatg agttagcaga agccttcag     600
aaggacttca caaatccac caaggaaagg cttctcttga ctgcgggcgt atctgcaggg     660
aggcaaatga ttgataacag ctatcaagtt gagaaactgg caaagatct  ggatttcatc     720
aacctcctgt cctttgactt ccatgggtct tgggaaaagc cccttatcac tggccacaac     780
agccctctga gcaagggtg gcaggacaga gggccaagct cctactacaa tgtggaatat     840
gctgtggggt actggataca taagggaatg ccatcagaga aggtggtcat gggcatcccc     900
acatatgggc actccttcac actggcctct gcagaaacca ccgtggggc ccctgcctct     960
ggccctggag ctgctggacc catcacagag tcttcaggct tcctggccta ttatgagatc    1020
tgccagttcc tgaaaggagc caagatcacg cggctccagg atcagcaggt tccctacgca    1080
gtcaagggga accagtgggt gggctatgat gatgtgaaga gtatgagac caaggttcag    1140
ttcttaaaga atttaaacct gggaggagcc atgatctggt ctattgacat ggatgacttc    1200
actggcaaat cctgcaacca gggcccttac cctcttgtcc aagcagtcaa gagaagcctt    1260
ggctccctgt gaaggattaa cttacagaga agcaggcaag atgaccttgc tgcctggggc    1320
ctgctctctc ccaggaattc tcatgtggga ttccccttgc caggatggcc tttggatctc    1380
tcttccaagc ctttcctgac ttcctcttag atcatagatt ggacctggtt ttgttttcct    1440
gcagctgttg acttgttgcc ctgaagtaca ataaaaaaaa ttcattttgc tccagt        1496
```

<210> SEQ ID NO 2
<211> LENGTH: 423
<212> TYPE: PRT
<213> ORGANISM: Homo sapiens

<400> SEQUENCE: 2

Gln His Leu Trp Leu Gly Ser Pro Asp Glu Val Trp Leu Tyr Leu Val
1               5                   10                  15

Cys Glu His Thr His Ile Phe Thr Ala Ile Ile Trp Asp Ser Arg Thr
            20                  25                  30

Arg Phe Gly Ser Thr Asp Phe Ser Phe His Pro Ser Ile Ala Gly Val
        35                  40                  45

```
Val Val Leu Leu Leu Gln Gly Gly Ser Ala Tyr Lys Leu Val Cys
 50                  55                  60

Tyr Phe Thr Asn Trp Ser Gln Asp Arg Gln Glu Pro Gly Lys Phe Thr
 65                  70                  75                  80

Pro Glu Asn Ile Asp Pro Phe Leu Cys Ser His Leu Ile Tyr Ser Phe
                 85                  90                  95

Ala Ser Ile Glu Asn Asn Lys Val Ile Ile Lys Asp Lys Ser Glu Val
            100                 105                 110

Met Leu Tyr Gln Thr Ile Asn Ser Leu Lys Thr Lys Asn Pro Lys Leu
        115                 120                 125

Lys Ile Leu Leu Ser Ile Gly Gly Tyr Leu Phe Gly Ser Lys Gly Phe
    130                 135                 140

His Pro Met Val Asp Ser Ser Thr Ser Arg Leu Glu Phe Ile Asn Ser
145                 150                 155                 160

Ile Ile Leu Phe Leu Arg Asn His Asn Phe Asp Gly Leu Asp Val Ser
                165                 170                 175

Trp Ile Tyr Pro Asp Gln Lys Glu Asn Thr His Phe Thr Val Leu Ile
            180                 185                 190

His Glu Leu Ala Glu Ala Phe Gln Lys Asp Phe Thr Lys Ser Thr Lys
        195                 200                 205

Glu Arg Leu Leu Leu Thr Ala Gly Val Ser Ala Gly Arg Gln Met Ile
    210                 215                 220

Asp Asn Ser Tyr Gln Val Glu Lys Leu Ala Lys Asp Leu Asp Phe Ile
225                 230                 235                 240

Asn Leu Leu Ser Phe Asp Phe His Gly Ser Trp Glu Lys Pro Leu Ile
                245                 250                 255

Thr Gly His Asn Ser Pro Leu Ser Lys Gly Trp Gln Asp Arg Gly Pro
            260                 265                 270

Ser Ser Tyr Tyr Asn Val Glu Tyr Ala Val Gly Tyr Trp Ile His Lys
        275                 280                 285

Gly Met Pro Ser Glu Lys Val Val Met Gly Ile Pro Thr Tyr Gly His
    290                 295                 300

Ser Phe Thr Leu Ala Ser Ala Glu Thr Thr Val Gly Ala Pro Ala Ser
305                 310                 315                 320

Gly Pro Gly Ala Ala Gly Pro Ile Thr Glu Ser Ser Gly Phe Leu Ala
                325                 330                 335

Tyr Tyr Glu Ile Cys Gln Phe Leu Lys Gly Ala Lys Ile Thr Arg Leu
            340                 345                 350

Gln Asp Gln Gln Val Pro Tyr Ala Val Lys Gly Asn Gln Trp Val Gly
        355                 360                 365

Tyr Asp Asp Val Lys Ser Met Glu Thr Lys Val Gln Phe Leu Lys Asn
    370                 375                 380

Leu Asn Leu Gly Gly Ala Met Ile Trp Ser Ile Asp Met Asp Asp Phe
385                 390                 395                 400

Thr Gly Lys Ser Cys Asn Gln Gly Pro Tyr Pro Leu Val Gln Ala Val
                405                 410                 415

Lys Arg Ser Leu Gly Ser Leu
            420

<210> SEQ ID NO 3
<211> LENGTH: 114
<212> TYPE: DNA
<213> ORGANISM: Artificial Sequence
<220> FEATURE:
<223> OTHER INFORMATION: 5' primer
```

-continued

<400> SEQUENCE: 3

```
cagcacctgt ggctggggag cccagatgaa gtgtggctct atcttgtatg tgagcacacc        60
cacattttca ctgccattat ctgggacagc agaaccaggt ttggctcaac agat             114
```